United States Patent [19]
Mears

[11] Patent Number: 6,066,147
[45] Date of Patent: May 23, 2000

[54] LIGATING STRUCTURE HAVING GREATER STRETCHABILITY, GREATER SHELF LIFE, AND GREATER LIGATING CHARACTERISTICS AND METHOD OF MANUFACTURE

[75] Inventor: Eric L. Mears, Duluth, Ga.

[73] Assignee: EnSurg, Inc., Norcross, Ga.

[21] Appl. No.: 09/044,483

[22] Filed: Mar. 19, 1998

[51] Int. Cl.[7] ................................................ A61B 17/00
[52] U.S. Cl. .............................................. 606/151; 433/11
[58] Field of Search ...................... 606/151, 157, 606/139, 144, 148, 232; 433/11, 18, 23, 15, 12; 623/11, 3

[56] References Cited

U.S. PATENT DOCUMENTS

| | | |
|---|---|---|
| 1,162,384 | 11/1915 | Nichols . |
| 1,352,470 | 9/1920 | Palmer . |
| 1,841,407 | 1/1932 | Gammeter . |
| 2,255,504 | 9/1941 | Current . |
| 2,717,023 | 9/1955 | Hetherington . |
| 3,697,348 | 10/1972 | Farnam . |
| 3,758,947 | 9/1973 | Kesling ........................................ 433/11 |
| 4,818,225 | 4/1989 | Fasnacht . |
| 4,900,250 | 2/1990 | Kesling et al. ............................ 433/11 |
| 5,378,146 | 1/1995 | Sterrett ........................................ 433/11 |
| 5,677,046 | 10/1997 | Fawley et al. . |
| 5,829,974 | 11/1998 | Brosius ........................................ 433/15 |

*Primary Examiner*—Michael Buiz
*Assistant Examiner*—Vikki Trinh
*Attorney, Agent, or Firm*—Sidley & Austin

[57] ABSTRACT

A ligating band is formed so as to have a pre-stress compression along its inner periphery and a pre-stress tension along its outer periphery at a free state, wherein all the material of the band is at a substantially equal tension when the band is subject to full circumferential expansion. In a free state, the inner periphery can buckle, at least partially filling an inner perimeter defined by the inner periphery with a plurality of material folds.

32 Claims, 2 Drawing Sheets

LIGATING STRUCTURE HAVING GREATER STRETCHABILITY, GREATER SHELF LIFE, AND GREATER LIGATING CHARACTERISTICS AND METHOD OF MANUFACTURE

FIELD OF THE INVENTION

The present invention relates to medical ligating bands characterized by an inner periphery that is significantly smaller than an outer periphery, and in particular, to medical ligating bands having enhanced stretchability, shelf life, and ligating characteristics.

BACKGROUND OF THE INVENTION

Medical elastic bands may be used for a plurality of procedures and tasks, for example, to supply force to orthodontic appliances and to ligate tissue. Medical elastic bands are commonly small and possess a relatively thicker material portion than other common elastic bands (e.g., common rubber bands). The inside diameter of a relaxed band is commonly only one-third of the band outer diameter. For at least these exemplary tasks, medical elastic bands act as energy storage devices. Specifically, energy is stored via the stretching of a free state elastic band, and the stored energy is "released" as the band contracts. For medical elastic bands required to have a long shelf life, it is important that, even near the end of such shelf life, that the elastic bands be capable of releasing maximum stored energy.

In ligation procedures, elastic bands are used to prevent fluid flow through ligated tissue. Ligating bands are typically dispensed from a ligating band dispenser, which may be fixed to the distal end of a hosting instrument, for example, an endoscope or ligating instrument. Ligating band dispensers are typically cylindrical and hollow in nature, where an inner diameter of the dispensers defines a cavity and an outer diameter carries one or more expanded ligating bands. Dispensers include a dispensing mechanism, allowing a user to remotely cause the dispensing of one or more ligating bands from the dispenser.

For a ligation procedure, a ligating band dispenser, mounted on an appropriate instrument, is positioned adjacent tissue targeted for ligation. Means are used to draw the tissue into the cavity defined by the inner diameter of the dispenser. These means may include suction, provided through a suction lumen which opens into the cavity, or a grasping device to grasp and physically draw tissue into the cavity region. Once the targeted tissue is properly positioned, the dispensing mechanism is actuated in such a manner so as to cause the dispensing of at least one ligating band. In the instant the ligating band is discharged from the dispenser, the dispensed ligating band attempts to return to its original, unexpanded dimensions, thus effectively ligating the targeted tissue. Subsequently, the means used to draw the tissue into the cavity region is ceased or disengaged, and the dispenser is moved away from the ligated tissue.

Where a ligating band is placed about, for example, a ballooning varix, polyp, hemorrhoids, or pre-cancerous lesion, the contracted ligating band induces fusion and healing in the base tissue and subjects the ligated tissue to necrosis. The necrotic tissue eventually separates from the surrounding tissue and simply passes into the human system. Alternatively, ligation may also be used for purposes of sterilization, wherein a ligating band may be placed over a folded loop portion of a Fallopian tube or a vas deferens to prevent the passage of internal reproductive fluids.

Conventional ligating bands (see FIG. 1) are formed from a highly elastic, homogenous elastomer material and typically assume a toroidal shape. Conventional bands for ligation of esophageal varices, as an example, have a relaxed inner diameter of approximately 1.8 mm and an outer diameter of 5.3 mm. When circumferentially expanded, these bands transition, as a whole, from neutral stress to tension. Circumferential expansion is limited to approximately seven times the bands' relaxed dimensions based on elastomer elongation strain limits.

Inherent to the shaping of these bands, the inner diameter of conventional ligating bands, being significantly smaller than the outer diameter, experiences significantly higher levels of strain, and therefore, stress, than an outer diameter when circumferentially expanded. Band material stretches and thins during elongation to a diameter many times the relaxed dimensions.

The multiple of strain and stress experienced by the inner diameter relative to the outer diameter of conventional ligating bands is approximately the ratio of the outer diameter to the inner diameter. In an expanded condition, the inner and outer diameters are nearly the same, or a ratio of one to one. In an unexpanded condition, the outer diameter is three times the inner diameter. For these bands, the strain and stress at the inner diameter will be three times greater than at the outer diameter when expanded. In other words, when the inner diameter of this conventional ligating band elongates seven times its relaxed dimensions (a maximum condition), for example, the outer diameter typically elongates less than three times its relaxed diameter. Accordingly, the inner diameter material is subjected to higher stresses than that of the outer diameter. This distribution of stresses is a limiting factor for enhancing elongation and ligation performance.

A further observation regarding the expansion characteristics of conventional ligating bands, the elongation of material at the outer diameter is typically less than one-half of its maximum elongation capability when the band is in a fully expanded condition. Conventional ligating bands therefore store less than maximum energy to ligate tissue, thus inefficiently utilizing the elastic material from which it is formed. To this end, larger bands of conventional construction are required to deliver the same degree of constriction as bands which maximize their energy storage potential.

Referring again the operational performance of conventional ligating bands in the context of stress and strain, in a fully expanded state, conventional ligating bands have a ratio of inner diameter to outer diameter of approximately 1:1. For this fully expanded state, the inner diameter of a conventional ligating band elongates approximately seven times its relaxed dimensions as compared to the outer diameter elongating less than three times its relaxed diameter. Consequently, the limited elongation of the outer diameter reveals that a majority of material near the outer diameter of a conventional band is utilized at less than 50% of its energy storage potential. In other words, while the inner diameter of a conventional ligating band fully utilizes its energy potential when expanded, such use drops to approximately 30% at the outer diameter of the band. Continued circumferential expansion following an inner diameter reaching a maximized energy storage potential can result in damage to the ligating band or breakage as the inner diameter becomes over-stressed.

As provided above, conventional ligating bands for ligation of esophageal varices have an original, relaxed inner diameter of approximately 1.8 mm. Conventional ligating bands are commonly pre-loaded and stored on a ligating band dispenser. Ligating band dispensers typically have an outer diameter of approximately 12.7 mm—representing a maximum stretched condition for conventional bands. Ligating bands may remain in this fully stretched condition for up to their full shelf life, for example, two years.

The duration of time in which the stored ligating bands are subjected to maximized internal stresses can result in permanent stretch, set, creep, or flow of material. While conventional ligating bands are originally incapable of ligating tissue having a cross-sectional area less than 2.54 mm$^2$, this area likely increases for ligating bands stored for extended periods on a ligating band dispenser. Given the relationship between stresses of the inner diameter and the outer diameter of conventional ligating bands (as well as the limitations of conventional materials), efforts to enhance ligating performance on smaller tissues through the reduction of the original, relaxed inner diameter results in a disproportionate reduction in the operational (or expansion) range of the ligating bands. Importantly, any such reduction in operational range would likely preclude such ligating bands from being used with conventional ligating band dispensers.

SUMMARY OF THE INVENTION

The present invention is directed to a ligating band for use in medical ligation procedures. In accordance with the present invention, the ligating band has an inner diameter region and an outer diameter region. This ligating band is capable of assuming at least two relative states: an unexpanded state, where the inner diameter region is in compression, and a fully (circumferential) expanded state, where all the material of the band is in substantially uniform tension.

In accordance with a ligating band of one embodiment of the present invention, in an unexpanded (or free) state, the inner perimeter, defined by the inner diameter region, is substantially filled with a plurality of material folds, thus creating a substantially closed inner perimeter. In a circumferentially expanded state, the inner perimeter assumes a diameter in proportion to a degree of circumferential expansion.

A method for fabricating ligating bands in accordance with the above structure includes forming an elastomer material to produce at least one band from the formed elastomer material, an unexpanded band having an outer diameter in tension and an inner diameter in compression. One example of such formation includes fully stretching an elastomer material, wrapping the stretched material about a mandrel, said mandrel having an outer diameter approximately equal to an expanded diameter of the ligating band so as to form unitary tubing, and cutting the unitary tubing into individual bands capable of assuming a small inner diameter in a free state.

An object of the present invention is to provide a ligating structure having improved ligating characteristics to enable tissue held within the confines of the structure to be held more securely, thereby promoting rapid healing and reducing the formation of scar tissue.

Another object of the present invention is to provide a small ligating structure to effect the required ligation force.

Another object of the present invention is to provide a ligating structure capable of achieving maximum expansion commensurate with the elastic properties of the structure material.

Another object of the present invention is to provide a ligating structure that minimizes maximum stress therein to improve shelf life and further minimize permanent stretch for common storage techniques.

Another object of the present invention is to provide a ligating structure subject to a substantially uniform stress when tension is maximized for stored energy efficiency.

Another object of the present invention is to provide a ligating structure which maximizes energy storage potential throughout all its material regions.

Another object of the present invention is to provide a ligating structure having an inner diameter filled with a plurality of folds or wrinkles when in a unexpanded state.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 1:
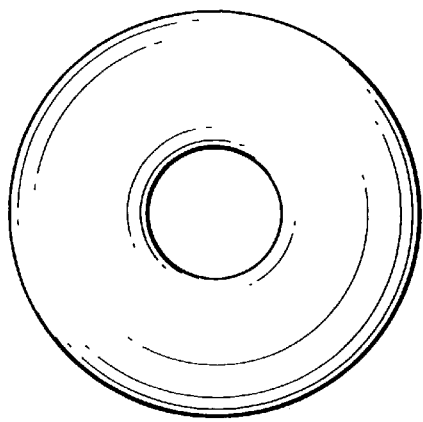
FIG. 1 is a plan view of a conventional ligating band.
Figure 2:
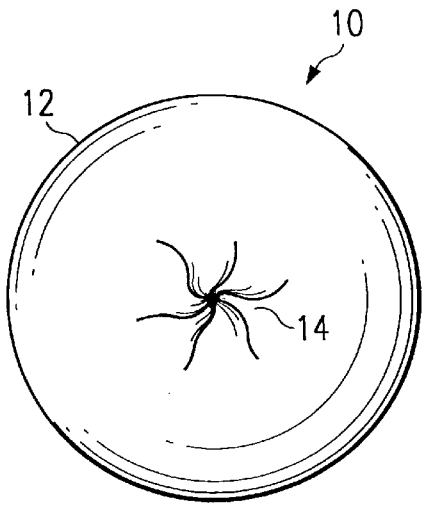
FIG. 2 is a plan view of a ligating structure in accordance with one embodiment of the present invention, where the ligating structure is in an unexpanded state.

FIG. 2 illustrates ligating structure 10 in accordance with the present invention. Structure 10 includes an outer periphery 12 and center portion 14 having an inner periphery. Ligating structure 10 is formed from those materials common to conventional ligating bands, for example, polyisoprene, natural rubber, polybutadiene, silicone, a blend of such materials, or the like.

Figure 3:
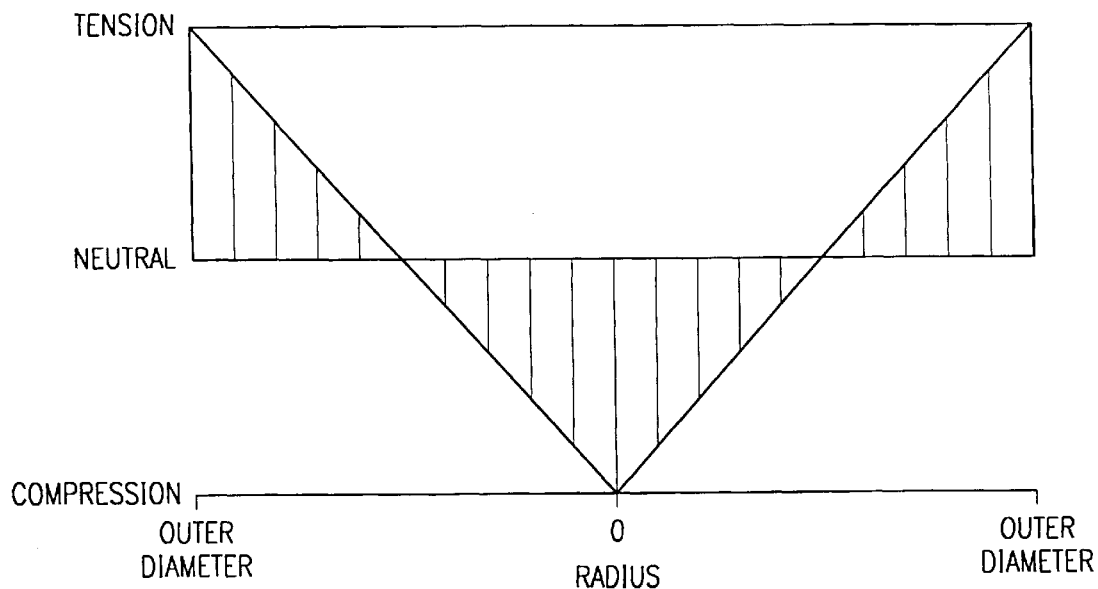
FIG. 3 graphically illustrates a first-order approximation of internal material stresses of the ligating structure of FIG. 2.

Unlike conventional ligating bands which are at a neutral stress throughout when unexpanded, an unexpanded ligating structure 10 has a compressive pre-stress along its inner periphery and a tension pre-stress along its outer periphery 12. FIG. 3 illustrates a first-order approximation of the pre-stress levels of ligating structure 10 when structure 10 is in an unexpanded state. The material of structure 10 is subject to an approximately uniform tension when fully expanded.

Figure 5:
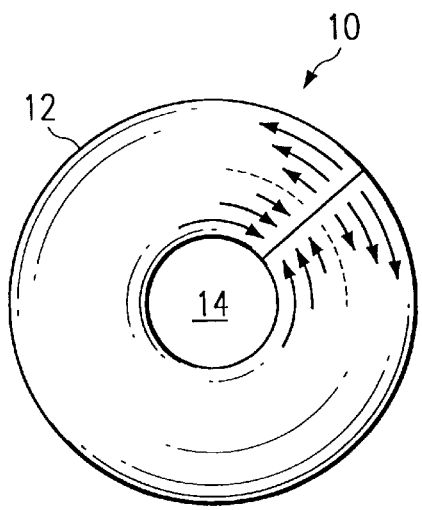
FIG. 5 is a plan view of a ligating structure in accordance with another embodiment of the present invention, where the ligating structure is in an unexpanded state.
Figure 4:
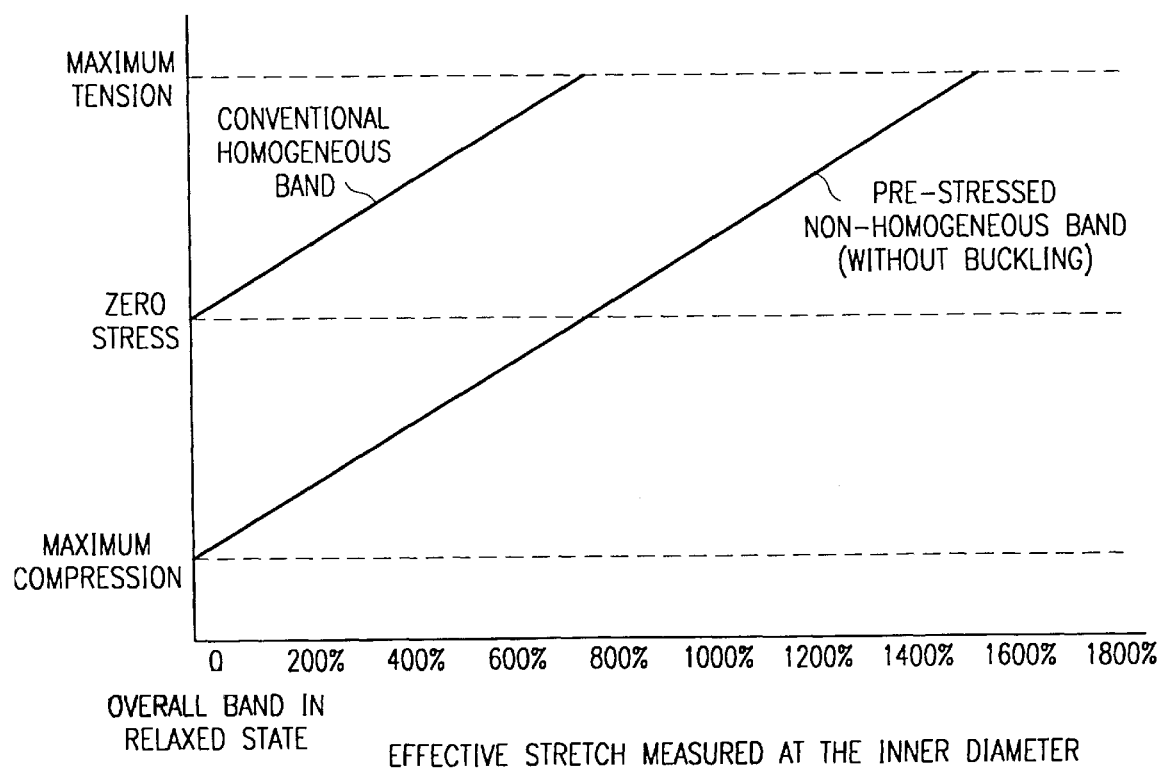
FIG. 4 is a graphical comparison of stretchability performance for a ligating band of the present invention and a conventional ligating band.

The pre-stress regions allow structure 10 to expand in accordance with at least the elastic properties of the material used to construct structure 10. Material used to form commonly used conventional ligating bands, as well as structure 10, can be stretched approximately seven times its relaxed dimensions. One embodiment, for example, a toroidal shape band exhibiting no buckling along its inner diameter in a free state (FIG. 5), may be circumferentially expanded approximately 15 tines its unexpanded inner diameter dimensions. FIG. 4 illustrates a comparison of the elastic performance, operating in pure circumferential expansion, for both that common within the art and this embodiment of the present invention.

For another embodiment, for example, a generally-toroidal shape band exhibiting buckling along its inner diameter region in a free state (FIG. 2) may be circumferentially expanded an approximately infinite amount with respect to its closed inner diameter.

The ability of structure 10 to readily expand 7–20+ times its unexpanded dimensions allows the storage of structures 10 on ligating band dispensers without concern of adverse affects attributable to, for example, permanent stretch, set, creep, or flow of material over a period equal to the shelf life of structure 10. Moreover, the geometry of structure 10, for example, mean diameter and thickness, may be altered to further optimize ligation, expansion, and storage stresses.

Returning to FIG. 2, it should be observed that structure 10 is shown having no inner diameter, thus seemingly forming a "disk." As the inner periphery of structure 10 is subjected to a pre-stress compression, when structure 10 is unexpanded (as shown), the region of material defining the inner periphery is caused to constrict toward a center point of structure 10. In other words, when compressive surface stresses along the inner periphery reach a critical buckling value, the inner periphery is caused to form folds and wrinkles, such folds and wrinkles filling the inner diameter. Of note, however, such buckling may not be as pronounced as illustrated in FIG. 2. Rather, compression along the inner periphery may result in a less-severe distortion of the inner diameter (i.e., from circular to non-circular) or no distortion of the inner diameter.

In addition to enabling the formation of a "zero-diameter" ligating band, the folds of an unexpanded center portion 14 serve to dynamically accommodate that tissue contained within the inner periphery of structure 10. Conventional ligating bands maintain a toroidal shape from an expanded state to a neutral stress state. Bodily tissue positioned within the inner periphery of a conventional ligating band will initially follow the inner periphery of the conventional ligating band through an initial portion of this transition; however, continued contraction will typically cause the encompassed tissue to buckle, creating internal folds and wrinkles. Voids created by such wrinkles and folds lessen the surface contact with the encompassing ligating band.

In contrast, the folds and wrinkles of center portion 14 of one embodiment of the present invention receive bodily tissue during advanced stages of contraction. During contraction of structure 10, tissue positioned within the inner periphery is simply guided by and will tend to follow the contracting inner surface. As the folds and wrinkles of center portion 14 assist in preventing voids between the inner periphery of structure 10 and the ligated tissue, structure 10 contacts ligated tissue over a greater surface area in comparison with conventional ligating bands.

Depending upon a selected material, ligating structure 10 may be formed by the follow processes:

(1) Highly-stretched, elastomer filaments or bands are wound, for example, in a helical or spiral wrapping pattern, about an oversized mandrel (i.e., a mandrel having an outer diameter greater than the mean diameter of a produced ligating band and approximately equal to an expanded inner diameter of the band). The filaments/bands are then allowed to fuse or are bonded or cured, thus creating a unitary tube. Individual ligating bands are formed by slicing the formed tube at regular intervals. The formed bands are removed from the mandrel, allowing the bands to constrict in a free state.

(2) At least two thin, elastomer tubes are formed on a mandrel in a well known manner, for example, dipping. Each tube is substantially equal in diameter, such diameter being consistent with the mean relaxed diameter of the final ligating structure 10. As a first step, one tube is inserted within the other tube. The concentric tubes are sufficiently expanded so that the inner diameter of the outer tube fully contacts the outer diameter of the inner tube. The tubes are fused, bonded, or cured in position in accordance with known methods. Individual ligating bands may then be produced by slicing the formed tube at regular intervals—producing bands having a rectangular-type cross-section. In a free state, the formed bands are allowed to constrict.

(3) Conventional ligating bands or tubing may be subjected to thermal processing (for example, cooling the inner surface of a tube of elastomer material while heating the outer surface of such tube) or chemical processing (for example, applying a plasticizer or the like to an inner surface of an elastomer tube or formed ligating band to produce swelling of the elastomer material along the inner surface) to induce the desired pre-stress regions therein.

(4) A thin tube of elastomer material is formed on a mandrel having an outer diameter substantially consistent with the mean relaxed diameter of the final ligating structure. The tube may be formed in a manner consistent with that described in example (2), above. Prior to removing the formed tube from the mandrel, the tube is partially cured, and more specifically, for a preferred embodiment, between 90% and 99% cured. Alternatively, the tube may be fully cured while on the mandrel. The tube is then rolled to form a toroidal band. To further the formation of material folds along an inner diameter, the mandrel may be subjected to a gentle rotation during rolling of the formed tubing and/or the mandrel may have a non-circular outer diameter. For the process in which the bands are only partially cured prior to rolling, once formed, the toroidal bands are subjected to the remaining cure period.

Curing modalities for the present invention are consistent with that well known in the art, for example, water baths, heat, forced air, and the like.

At least with forming examples one and two above, a central region of formed structure 10 is at neutral stress when in a free state. Upon full circumferential expansion of structure 10, this central region is in tension, such tension being substantially equal to that of the expanded inner and outer peripheries. The position of the central region, relative to the structure 10, will differ for each embodiment, for example, a filled inner diameter (FIG. 2), a partially-filled or non-circular inner diameter (FIG. 5), or a smooth inner diameter (not shown).

Ligating structures 10 have an inner diameter ranging from a substantially closed center portion 14 (i.e., a pinhole) to approximately 80% of the outer diameter in a free state. Consistent with conventional ligating bands, ligating structures 10 used in esophageal ligation have an outer diameter of approximately 5.3 mm in such free state.

While a conventional ligating band could be molded or formed with a plurality of folds and wrinkles, providing a near-zero diameter similar to that of the present invention, one skilled in the art shall understand that for such construction, the inner diameter of the ligating band would be subject to non-uniform expansion characteristics, thus differing somewhat from the descriptions provided above. Regardless, however, such convention would offer certain benefits consistent with the present invention and serve as an improvement over that known.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. An elastic medical ligating band, having an inner diameter region defining an inner perimeter and an outer diameter region defining an outer diameter, formed so that in a fully circumferentially expanded state all the material of the band is in substantially uniform tension,
    wherein the inner perimeter is 80% or less of the outer diameter in a free state.

2. An elastic medical ligating band in accordance with claim 1, wherein in a free state, the inner diameter region has a substantially buckle-free inner perimeter.

3. An elastic medical ligating band in accordance with claim 1, wherein in a free state, the inner diameter region is buckled, thus forming a non-circular inner perimeter.

4. An elastic medical ligating band in accordance with claim 3, wherein the inner perimeter is substantially filled with a plurality of material folds.

5. An elastic medical ligating band having an inner diameter region and an outer diameter region, formed so that in an unexpanded state, the inner diameter region is in compression, and in a fully circumferentially expanded state, all the material of the band is in substantially uniform tension.

6. An elastic medical ligating band in accordance with claim 5, wherein in the unexpanded state, the inner diameter region is buckled.

7. An elastic medical ligating band in accordance with claim 6, wherein an inner perimeter, defined by the inner diameter region, is non-circular.

8. An elastic medical ligating band in accordance with claim 5, wherein the inner diameter region defines an inner perimeter and the outer diameter region defines an outer diameter, the inner perimeter being 80% or less of the outer diameter in a free state.

9. An elastic medical ligating band having an inner diameter region and an outer diameter region, formed so that in an unexpanded state, the inner diameter region is in compression and the outer diameter region is under tension, and in a fully circumferentially expanded state, all the material of the band is in substantially uniform tension.

10. An elastic medical ligating band in accordance with claim 9, wherein in the unexpanded state, the inner diameter region is buckled.

11. An elastic medical ligating band in accordance with claim 10, wherein an inner perimeter, defined by the inner diameter region, is non-circular.

12. An elastic medical ligating band in accordance with claim 9, wherein the inner diameter region defines an inner perimeter and the outer diameter region defines an outer diameter, the inner perimeter being 80% or less of the outer diameter in a free state.

13. An elastic medical ligating band formed from an elastomer material and having an inner diameter region and an outer diameter region, formed so that in an unexpanded state, the inner diameter region is substantially filled with a plurality of material folds, and in a circumferentially expanded state, the inner diameter region is progressively cleared of the material folds and defines an inner perimeter proportionate to a degree of circumferential expansion.

14. An elastic medical ligating band in accordance with claim 13, wherein the outer diameter region defines an outer diameter, the inner perimeter being 80% or less of the outer diameter in a free state.

15. An elastic medical ligating band having an inner periphery region defining an inner diameter and an outer periphery region defining an outer diameter, wherein at least one projection extends inwardly from the inner periphery region and terminates within a region defined by the inner diameter.

16. An elastic medical ligating band in accordance with claim 15, wherein the inner periphery region is in compression when in a free state and subject to buckling, and the inwardly-protruding material is a plurality of material folds produced by such buckling.

17. An elastic medical ligating band, having an inner periphery defining an inner perimeter and an outer periphery defining an outer diameter, formed so that any arcuate section at a free state has a first length extending along an inner periphery of that section and a second length extending along an outer periphery of that section,
    wherein the first length and the second length are substantially equal, and
    wherein the inner perimeter is 80% or less of the outer diameter when in an unexpanded state.

18. A method of ligating tissue, comprising the steps of:
    providing an expanded ligating band having an inner periphery defining an inner perimeter and an outer periphery defining an outer diameter, formed so that in a fully circumferentially expanded state all the material of the band is in substantially uniform tension, and in a free state, the inner perimeter is 80% or less of the outer diameter
    positioning targeted tissue within the inner perimeter; and
    releasing the ligating band so that the ligating band is allowed to constrict about the targeted tissue.

19. A method in accordance with claim 18, wherein the inner periphery of the ligating band is capable of circumferential expansion of at least 7–20 times greater than the inner perimeter when unexpanded.

20. A method in accordance with claim 19, wherein an area defined by the inner perimeter is less than 2.54 mm$^2$ in the free state.

21. A method in accordance with claim 18, wherein during constriction, the inner periphery transitions from tension to compression.

22. A method in accordance with claim 18, wherein the ligating band, when constricted, forms a plurality of folds along the inner periphery.

23. A method in accordance with claim 22, wherein when the ligating band constricts about the targeted tissue, the plurality of folds accommodate an interposition of tissue between each of the plurality of folds.

24. A method in accordance with claim 18, wherein the inner periphery buckles when the ligating band constricts.

25. A method in accordance with claim 24, wherein a fully constricted ligating bands has a non-circular inner perimeter.

26. A method of ligating tissue, comprising the steps of:
    providing an expanded ligating band having an inner periphery defining an inner perimeter and an outer periphery defining an outer diameter, wherein the inner perimeter is at least partially filled with inwardly-protruding material, and in a free state, the inner perimeter is 80% or less of the outer diameter
    positioning targeted tissue within the inner perimeter; and
    releasing the ligating band so that the ligating band is allowed to constrict about the targeted tissue.

27. A method in accordance with claim 26, wherein the inner periphery of the ligating band is capable of circumferential expansion of at least 7–20 times greater than the inner perimeter when unexpanded.

28. A method in accordance with claim 27, wherein an area defined by the inner perimeter is less than 2.54 mm$^2$ in the free state.

29. A method in accordance with claim 26, wherein during constriction, the inner periphery transitions from tension to compression.

30. A method in accordance with claim 26, wherein the inwardly-protruding material forms a plurality of folds.

31. A method in accordance with claim 30, wherein when the ligating band constricts about the targeted tissue, the plurality of folds accommodate an interposition of tissue between each of the plurality of folds.

32. A method in accordance with claim 26, wherein the inner periphery buckles when the ligating band constricts.

* * * * *